United States Patent
Newill

(10) Patent No.: US 9,704,411 B1
(45) Date of Patent: Jul. 11, 2017

(54) METHOD AND APPARATUS FOR DETERMINING READING ACUITY WITH AUTOMATED CALIBRATION

(71) Applicant: Edward Newill, Little Neck, NY (US)

(72) Inventor: Edward Newill, Little Neck, NY (US)

(*) Notice: Subject to any disclaimer, the term of this patent is extended or adjusted under 35 U.S.C. 154(b) by 785 days.

(21) Appl. No.: 13/955,790

(22) Filed: Jul. 31, 2013

(51) Int. Cl.
*A61B 3/032* (2006.01)
*G09B 17/00* (2006.01)
*A61B 3/00* (2006.01)

(52) U.S. Cl.
CPC .......... *G09B 17/003* (2013.01); *A61B 3/0058* (2013.01); *A61B 3/032* (2013.01)

(58) Field of Classification Search
CPC ........... A61B 3/02; A61B 3/032; A61B 3/028; A61B 3/10; A61B 3/113; A61F 2009/00846
USPC ....... 351/200, 203, 205, 208, 209, 210, 211, 351/222, 223, 246; 434/156, 176, 178, 434/179, 180, 184
See application file for complete search history.

(56) References Cited

U.S. PATENT DOCUMENTS

| | | | |
|---|---|---|---|
| 5,568,209 A | 10/1996 | Priester et al. | |
| 6,072,443 A | 6/2000 | Nasserbakht et al. | |
| 6,543,898 B1 | 4/2003 | Griffin et al. | |
| 6,715,878 B1 | 4/2004 | Gobbi et al. | |
| 7,033,025 B2 | 4/2006 | Winterbotham | |
| 7,427,135 B2 | 9/2008 | Chen et al. | |
| 7,430,365 B2 | 9/2008 | Ng et al. | |
| 7,695,138 B2 | 4/2010 | Ng et al. | |
| 7,878,652 B2 | 2/2011 | Chen et al. | |
| 8,240,851 B2 | 8/2012 | Reichow et al. | |
| 8,337,019 B2 | 12/2012 | Murray et al. | |
| 2001/0026352 A1 | 10/2001 | Ohyagi | |
| 2003/0048414 A1 | 3/2003 | Nagayama et al. | |
| 2003/0218721 A1 | 11/2003 | Stern et al. | |

(Continued)

FOREIGN PATENT DOCUMENTS

EP 2061369 B1 12/2011
WO 2008064379 A1 6/2008

OTHER PUBLICATIONS

Dexl et. al., "Reading performance after implantation of a small-aperture corneal inlay for the surgical correction of presbyopia: Two-year follow-up"; J Cateract Refract Surg 2011; 37; 525-531.*

(Continued)

*Primary Examiner* — Scott J Sugarman
*Assistant Examiner* — Robert E Tallman
(74) *Attorney, Agent, or Firm* — Simpson & Simpson, PLLC

(57) ABSTRACT

A method and apparatus for calculating a log MAR value for a reading acuity test, including the steps of displaying words on a first computer monitor, where the words will be read aloud by a person taking the test; displaying the words on a second computer monitor, where words will be observable by a person administering the test, where the administrator can select words which are incorrectly read using a pointing device; measuring the amount of time the first person takes to read the words; calculating the reading rate based upon both the words correctly and those read incorrectly; measuring the distance between the first person and the monitor; and, calculating the log MAR value based upon the distance, the font size and the reading rate.

9 Claims, 11 Drawing Sheets

(56) References Cited

U.S. PATENT DOCUMENTS

| | | |
|---|---|---|
| 2005/0041208 A1 | 2/2005 | Winterbotham |
| 2006/0078858 A1* | 4/2006 | Vroman .................. A61B 5/16 |
| | | 434/179 |
| 2010/0253913 A1* | 10/2010 | Artal Soriano ........ A61B 3/032 |
| | | 351/223 |
| 2011/0001924 A1 | 1/2011 | Giraudet et al. |
| 2011/0157550 A1 | 6/2011 | Chen et al. |
| 2012/0050685 A1 | 3/2012 | Bartlett et al. |
| 2012/0075586 A1 | 3/2012 | Kirschen et al. |
| 2012/0154751 A1* | 6/2012 | Pelah .................. A61B 3/0041 |
| | | 351/224 |
| 2012/0300173 A1 | 11/2012 | Reichow et al. |

OTHER PUBLICATIONS

Colenbrander, August, MD. "Introduction to Visual Acuity Measurement," Precision Vision, 2008, San Francisco, California.

\* cited by examiner

Patient Search - Version 8.4.1

Search Criteria
Patient ID:
Last Name: [SEARCH]

| 1234 | John Smith |
| 5678 | Alice Brown |
| 1357 | Tim Tester |

Patient Data

Last Name:
First Name:
Birth Date: (dd-mm-yyyy)
Study:
Investigator:
Operation Date: (dd-mm-yyyy)

Perform SRD Exam
Perform FRACT Exam
Close Window

Phase:
Control Subject? ● NO ○ YES
Notes

Add New Patient
(Enter Data First)

Clear Patient Data Screen
To ADD a new patient click the 'Clear Patient Data Screen' button, type in the new information, then click the 'Add New Patient' button.

Choose Exam Data to Display
● SRD
○ FRACT

SRD VISION

Update Refraction Data
Print SRD Report

Export SRD Data 300
310
302
304

METHOD AND APPARATUS FOR DETERMINING READING ACUITY WITH AUTOMATED CALIBRATION

TECHNICAL FIELD

The invention relates generally to visual acuity tests. More specifically, the invention relates to a system and method for determining reading acuity and to a system that presents sentences on a screen with a variable letter size, and, even more specifically, to a system that randomizes the sentences presented on the screen, adjusts the reading speed to accommodate for misread words and automatically calibrates distance measurements before determining reading acuity.

REFERENCE TO COMPUTER PROGRAM LISTING APPENDIX

The present application includes a computer program listing appendix. The appendix contains an ASCII text function of the computer program listing or sample file input data as follows:

| | | |
|---|---|---|
| form1SRD-codeforrandomizationofsentences.txt | 3 KB | Created Jul. 10, 2013 |
| form1SRDcodeforwordverification.txt | 5 KB | Created Jul. 10, 2013 |
| FormAutoCalibrate-codeforAuto-calibrationofdistance.txt | 10 KB | Created Jul. 10, 2013 |

BACKGROUND

Visual acuity is the acuteness or sharpness of a person's vision. In the 19$^{th}$ century, Franciscus Donders defined visual acuity as the magnification needed to perform as well as the standard eye. It was believed that the standard eye could recognize letters that subtend an angle of 5' of arc at a given distance, usually 20 feet. The magnification needed was calculated first by dividing the size of letters visualized by a patient by the size of letters visualized by the standard eye. The reciprocal of the magnification needed equaled the visual acuity. In 1862, Hermann Snellen and Donders introduced the letter chart, also known as the Snellen chart, which is still used today to measure visual acuity. The traditional Snellen chart is printed with eleven lines of block letters. The first line consists of one very large letter and each subsequent row has additional letters; each row decreases in size. A person taking the test covers one eye and reads aloud the letters of each row. The smallest row that can be read accurately indicates the visual acuity in that eye. The letters on an acuity chart are formerly known as optotypes. Wall-mounted Snellen charts are inexpensive and are used to approximate visual acuity, such as, for children in a school nurse's office.

Sometimes however, visual acuity approximations are insufficient and more careful assessments are needed, for example, during an eye examination performed by a doctor evaluating a patient's diabetic retinopathy. More exact visual acuity tests can be performed with equipment such as computers. For example, U.S. Pat. No. 8,240,851 (Reichow et al.) discloses a computerized system for testing a person's visual ability including a presenting component, an input component arranged to receive input provided by a patient, and a processing component configured to process the user's input. Others use the logarithm of the minimum angle of resolution (log MAR) to measure visual acuity. In these tests, the sizes of the letters progress systematically in geometric progression. In contrast to the Snellen chart, the space between lines and letters change in proportion so that the effect of contour interaction is constant. Log MAR charts include five letters on each line as opposed to the Snellen chart.

Measuring visual acuity requires knowing the size of the letters or optotypes tested, the distance between the patient and the letters or optotypes tested, and the patient's ability to accurately perceive the letters or optotypes. The near vision determined with respect to reading a text is also referred to as reading acuity. To test reading acuity, it is further required to know the speed at which the patient can accurately read the tested sentences.

European Patent Application No. EP07815184 discloses a device for determining the near vision acuity for reading text and the recognition of graphic illustrations by a patient. The teachings of European Patent Application No. EP07815184 are incorporated herein by reference in its entirety. The disclosed device includes a presentation surface on which a number of texts or various sizes can be displayed, a microphone for recording feedback from the patient when reading the texts, and a computer system set up for monitoring the reading process based on the microphone recordings and for determining the patient's near vision or reading acuity in relation to the still legible font size. The patented invention discloses a proposed means for measuring the reading distance freely selected by the patient to the text presented to the patient on the presentation surface. The computer system of the invention disclosed includes cameras to detect the presence of the reader's face by detecting a sensor placed in between the reader's eyes via infrared technology. The cameras are manually calibrated to detect how far the sensor on the reader's face is from the text/graphics using a ruler. This manual process is tedious and time consuming. Unfortunately, Reichow et al. discussed above do not disclose a means for automatically calibrating a distance measured between a patient and the presentation component of the device of the invention.

Therefore, there is a long-felt need for an improved method and apparatus for testing near vision acuity with automated calibration. There is also a long-felt need for a system and method for determining reading acuity that randomizes the sentences presented on a screen and adjusts the reading rate calculation to accommodate for misread words.

SUMMARY

A computer-based system for calculating a log MAR value for a reading acuity test, comprising: means for displaying a plurality of words in a font size on a first computer monitor, where the plurality of words will be read aloud by a first person taking the test; means for displaying a copy of the plurality of words on a second computer monitor, where the plurality of words will be observable by a second person, and each of the plurality of words is selectable by the second person using a pointing device, such that the second person may select any of such words that are read incorrectly by the first person; means for measuring the amount of time the first person takes to read the plurality of words on the first computer monitor; means for calculating a reading rate based upon the plurality of words and the amount of time, where the reading rate is modified in accordance with the number of words selected by the second person as read incorrectly; means for measuring the distance between the first person and the first monitor; and, means for calculating the log MAR value based upon the distance, the font size and the reading rate.

A computer-based system for calculating a log MAR value for a reading acuity test, comprising: means for selecting a sentence randomly from an inventory of sentences; means for displaying the sentence in a font size on a first computer monitor, where the sentence will be read aloud by a first person taking the test; means for displaying a copy of the sentence on a second computer monitor; means for measuring the amount of time the first person takes to read the sentence on the first computer monitor: means for calculating a reading rate based upon the sentence and the amount of time; means for measuring the distance between the first person and the first monitor, means for calculating the log MAR value based upon the distance, the font size and the reading rate.

The present invention also comprises a method of calculating a log MAR value for a reading acuity test, comprising the steps of displaying a plurality of words in a font size on a first computer monitor, where the plurality of words will be read aloud by a person taking the test; displaying a copy of the plurality of words on a second computer monitor, where the plurality of words will be observable by a second person, and each of the plurality of words is selectable by the second person using a pointing device, such that the second person may select any of such words that are read incorrectly by the first person; measuring the amount of time the first person takes to read the plurality of words on the first computer monitor; calculating a reading rate based upon the plurality of words and the amount of time, where the reading rate is modified in accordance with the number of words selected by the second person as read incorrectly; measuring the distance between the first person and the first monitor; and, calculating the log MAR value based upon the distance, the font size and the reading rate.

The present invention also comprises a method of calculating a log MAR value for a reading acuity test, comprising the following steps: displaying a plurality of words in a font size on a first computer monitor, where the plurality of words will be read aloud by a person taking the test; displaying a copy of the plurality of words on a second computer monitor, where the plurality of words will be observable by a second person, and each of the plurality of words is selectable by the second person using a pointing device, such that the second person may select any of such words that are read incorrectly by the first person; measuring the amount of time the first person takes to read the plurality of words on the first computer monitor, calculating a reading rate based upon the plurality of words and the amount of time, where the reading rate is modified in accordance with the number of words selected by the second person as read incorrectly; measuring the distance between the first person and the first monitor; and, calculating the log MAR value based upon the distance, the font size and the reading rate.

A computer-based system for calculating a log MAR value for a reading acuity test, comprising: means for displaying a plurality of words in a font size on a first computer monitor, where the plurality of words will be read aloud by a first person taking the test; means for displaying a copy of the plurality of words on a second computer monitor, means for measuring the amount of time the first person takes to read the plurality of words on the first computer monitor; means for calculating a reading rate based upon the plurality of words and the amount of time; means for measuring the distance between the first person and the first monitor; means for automatically calibrating the means for measuring the distance between the first person and the first monitor; and, means for calculating the log MAR value based upon the distance, the font size and the reading rate.

A general object of the present invention is to provide an apparatus for administering visual acuity tests that can be automatically calibrated.

Another object of the present invention is to provide a method and apparatus for administering visual acuity tests that randomizes the sentences displayed during an exam and to avoid presenting a sentence that was recently presented.

A further object of the present invention is to provide a method and apparatus for measuring visual acuity that graphically displays unique sentences randomly to prevent familiarization.

These and other objects, advantages and features of the present invention will be better appreciated by those having ordinary skill in the art in view of the following detailed description of the invention in view of the drawings.

BRIEF DESCRIPTION OF THE DRAWINGS

The nature and mode of operation of the present invention will now be more fully described in the following detailed description of the invention taken with the accompanying figures, in which:

FIG. 7A is a screen shot of the patient search window;

FIG. 7B is a screen shot of the patient search window with a patient selected and the "Perform SRD Exam" button enabled; and, FIG. 8 is a screen shot of the Perform Exam window.

DETAILED DESCRIPTION

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspect. The present invention is intended to include various modifications and equivalent arrangements within the spirit and scope of the appended claims.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

By "graphical user interface" (hereinafter "GUI") we mean an interface between a user and a computer system. By "GUI device" we mean computer hardware used to implement an interface between a user and a computer system, including, but not limited to a mouse as a pointing device, a keyboard, a touch screen, motion recognition systems, and audio recognition systems. A GUI device can function to receive input from a user and to provide output, for example to a user. A GUI device also can function as a display device, for example providing audio and visual representations.

By "MAR" in "log MAR" we mean Minimum Angle of Resolution. The log MAR value is a visual acuity value as a measure of visual acuity loss using a linear scale.

Figure 1:
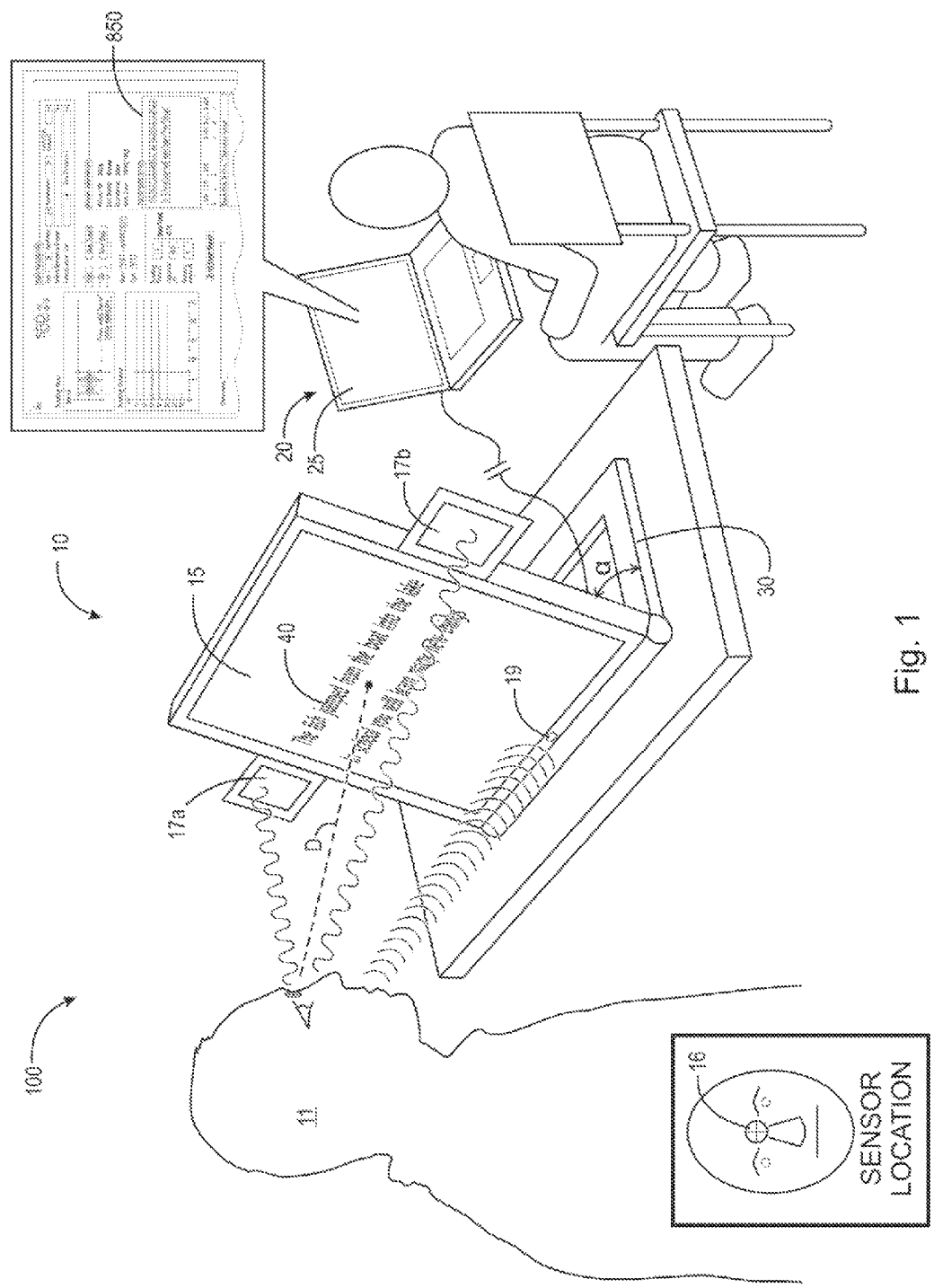
FIG. 1 illustrates an embodiment of the invention in use during an exam.

Referring now to the Figures, FIG. 1 illustrates a computer-based system 100, also referred to as "Salzburg Reading Desk" or SRD in reference to its place of origin, in use during an exam to determine ready acuity. During an exam, display component 10 is positioned in front of subject 11 (referred to as "a first person" in the Claims below) and computer 20 is positioned in front of an operator (referred to as "a second person" in the Claims below) administering the exam. Display component 10 is preferably placed on a flat surface, such as a table, that has an adjustable height or subject 11 is allowed to sit on a chair with an adjustable height in order to allow subject 11 to read off of monitor 15 at a comfortable height. Computer 20 has monitor 25 (referred to as "a second monitor" in the Claims below) is preferably placed out of the line of sight of subject 11 during the exam in order to minimize the number of distractions.

Display component 10 generally includes monitor 15 (referred to as "a first monitor" in the Claims below), cameras 17a and 17b, microphone 19 and base 30. Monitor 15 is pivotally secured to base 30 with a friction hinge such that reading angle $\alpha$, which is also referred to as the angle of inclination of monitor 15, is adjustable. The friction hinge enables subject 11 to adjust angle $\alpha$ of monitor 15, preferably between 0° and 90°, so that the exam can be administered under realistic conditions such as reading at a freely selectable, subjectively comfortable reading distance. However, angle $\alpha$ can be restricted to adjustment between 0° and 40° in another embodiment. Angle $\alpha$ is transmitted as an input to computer 102 via cameras 17a and 17b. Alternatively, angle $\alpha$ can be transmitted via a pitch meter mounted on the underside of monitor 15 or via an angle sensor by means of a flexible spindle.

For a single data run, monitor 15 displays a visual indicium, preferably sentences, to test subject 11. However, other templates of visual indicia can also be used such as a text character, a word or paragraph. Other templates can comprise a variety of suitable symbols or graphic illustrations, such as, e.g., numbers, figures, tumbling E's, Landolt rings, characters from different languages, musical notes, maps, city maps, time tables, images for children which can be displayed among other things on monitor 15. Subject 11 reads the text on monitor 15, and a reading acuity is determined on this basis. Visual indicium 40 is displayed on monitor 15 with a designated font size, also referred to as the letter size, and is controlled by the operator for each data run of an exam.

In addition, system 100 comprises a device to determine reading distance D during a single data run, preferably realized by means of cameras 17a and 17b placed on either side of monitor 15. Reading distance D is the distance between tag 16 placed between the subject's eyes just above the bridge of his or her nose or on his or her eye glasses, and monitor 15.

Preferably, tag 16 takes the form of a colorful adhesive dot with luminous day paint with a diameter of 12 mm, and cameras 17a and 17b are infrared cameras. However any fiducial marker compatible with cameras 17a and 17b can be used. The reading distance is calculated based on the set angle $\alpha$, and taking into account the geometric arrangement of cameras 17a and 17b by means of photogrammetry. However, system 100 is not restricted to the photogrammetric measurement of the respective reading distance freely selectable by subject 11; in fact, it can be determined with any other suitable method, for example acoustically by means of ultrasound. The reading distance is measured, preferably during the reading process from vertical and horizontal displacement values of tag 16 with cameras 17a and 17b, and a distance-corrected reading acuity is calculated based on the reading distance and font size of the respective text.

Cameras 17a and 17b are provided at a well-defined arrangement relative to monitor 15. They are aligned in such a way that they both cover the area of the room taken up by the subject's head. The optical main axes of the cameras are preferably at a horizontal level. The spatial coordinates of tag 16, such as vertical and horizontal displacement values, and subsequently the distance of tag 16 from the text to be read are calculated based on the image coordinates of the object point that represents tag 16. For this purpose, the object point characterized by the special color of tag 16 is identified in every image. The center point of the identified color range is used as a results coordinate. The results coordinates of both camera images are used to determine the position of tag 16 in relation to the camera positions according to the known stereo imaging method. This information is used to calculate the respective reading distance based on the known positional relation among the cameras 17a and 17b and monitor 15, whose position is accurately known in connection with the knowledge of the inclination through angle $\alpha$. Cameras 17a and 17b are preferably infrared USB cameras which communicate with computer 20 via USB ports.

Furthermore, the current invention 100 includes microphone 19 used to measure the duration of the reading process. Microphone 19 is integrated in display component 10 to record the subject's language and to accurately determine the respective duration the subject needs for reading. The control/measuring software can use this information to calculate a reading rate in words per minute and characters per minute.

Microphone 19 is connected to an acoustic threshold value switch to determine when subject 11 is talking. A sound wave registered at a value greater than the acoustic threshold determines a temporal starting point and a pause in the speech lasting for an extended period of time, for example for several seconds, is interpreted as the temporal stopping point of the reading procedure. The pause in the speech indicating the end of the reading procedure should be for an extended period of time because short pauses can be due to normal speech pauses such as taking a breath or speaking silent sounds. The time between the temporal starting point and the temporal stopping point defines the reading duration.

In an embodiment, a signal button can be provided instead of or in addition to the acoustic threshold value switch. It will be used by the subject (e.g., if the subject is deaf or speech impaired) to signal the reading time, for example by pressing the signal button at the beginning and the end of reading a text. Furthermore, the measuring procedure can essentially be performed without a control person, if a signal button is used, within the meaning of automating the experiment sequence. In addition, an optical signal (signal lamp) can be provided, in particular to signal the start of the measuring procedure to hearing-impaired subjects. In other words, this optical signal can be used in addition to the acoustic start signal of the reading procedure.

Monitor 15, and if desired also the entire component 10, can additionally be surrounded by a peep-type case (not illustrated), which can also be realized as a tunnel-shaped cover. This prevents the dealignment of the cameras. In addition, it allows the use of the device irrespective of the surrounding illumination, in particular with respect to the power, color and frequency of the extraneous light. Furthermore, it also prevents impairments of cameras 17a and 17b for example by reflection on the subjects clothing.

The operator uses computer 20 to control the presentation of sentences and other possible optotype charts and visual indicia on monitor 15, as well as to control other exam parameters such as screen luminance and contrast. Computer 20 has software that is secure for the privacy of patients for managing the names of patients and their acuity data if an eye care professional would chose to save this data.

An exam to determine visual acuity, generally includes a succession of data runs, controlled by the operator, of displaying visual indicia to subject 11 on monitor 15 in gradually smaller sized heights or fonts to mimic an analysis of reading acuity based on Reading Charts. Every paragraph of a typical Reading Chart contains a sentence, comprising 14 words arranged on 3 lines. The character sizes of the reading charts are graduated according to a geometric series, namely with a factor of $10^{0.1}$. Log MAR values are assigned to the reading charts which correspond to the scaled logarithm of the character size. Consequently, the Log MAR values are linear, for example from 0.9 (largest font size) to −0.2 (smallest font size) for a reading distance of 40 cm. The current invention can display sentences with a variable number of words on a variable number of lines.

Figure 2:
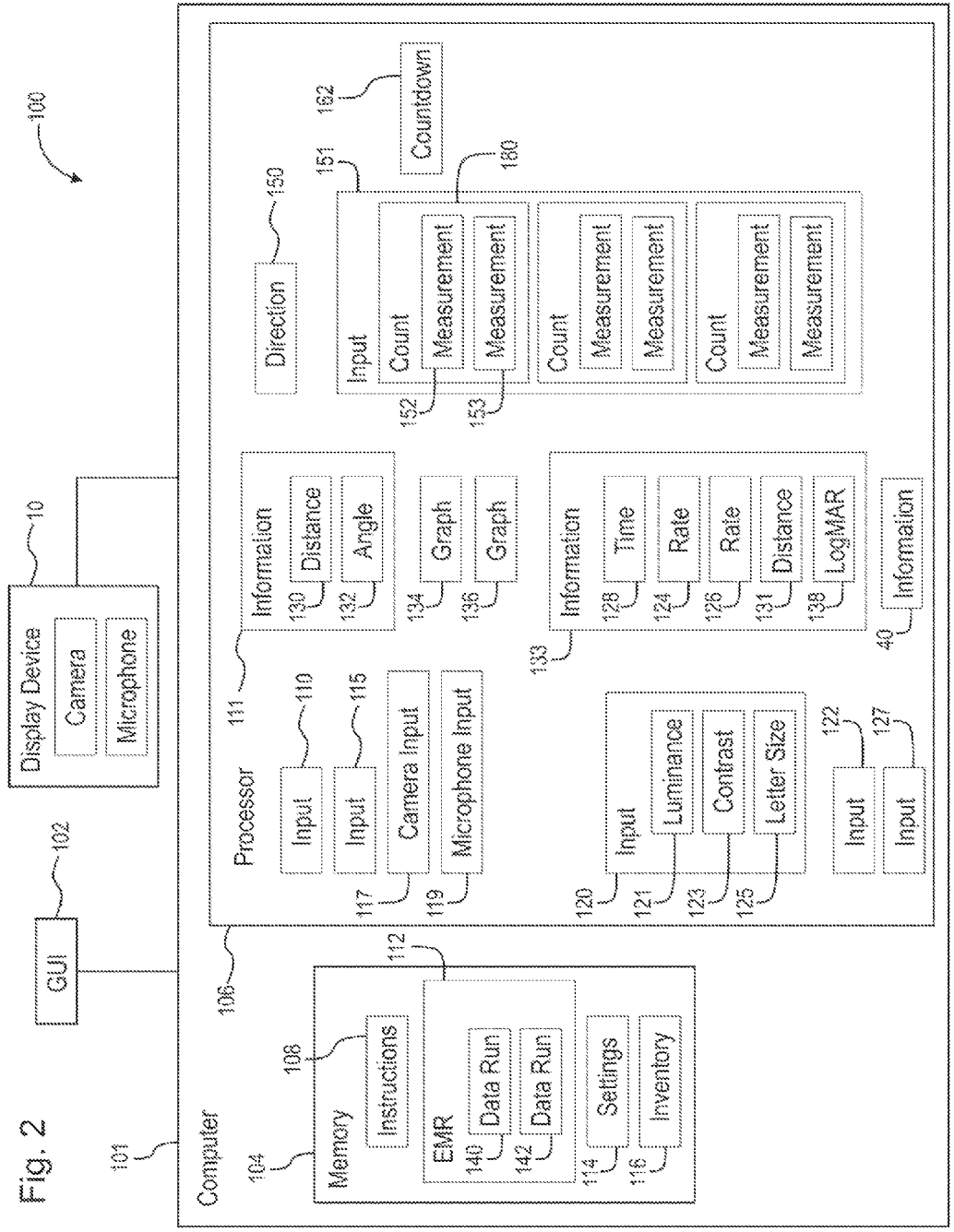
FIG. 2 is a schematic block diagram of the present invention.

FIG. 2 is a schematic block diagram of computer-based apparatus 100 for determining reading acuity. Apparatus 100 includes at least one computer 101 with at least one memory unit 104. and at least one processor 106. Memory unit 104 is configured to store computer readable instructions 108. Processor 106 is configured to execute the computer readable instructions to receive input 110 identifying a subject and access electronic medical record (hereinafter "EMR") 112 for the subject. Input 110 can be provided by the subject to the operator for inputting to computer 101 through GUI device 102. In an example embodiment, EMR 112 is stored in unit 104; however, it should be understood that the EMR can be stored in a different memory unit.

Memory unit 104 is configured to store computer readable instructions 108, EMR 112 of the subject, and inventory 116 of visual indicia, preferably sentences. EMR 112 can also include multiple data runs such as data runs 140 and 142 of a reading acuity exam if the operator chooses to do so. In an embodiment, memory unit 104 is configured to store a plurality of inventories of visual indicia, as will be described in more detail below. Memory unit 104 is also configured to store settings 114, which can include values such as default reading distance values and accuracy level values required to calibrate any measurement values provided by camera input 117.

Hereinafter, it is understood that "processor 106 is configured to" is analogous to "processor 106 is configured to execute computer readable instructions 108 to". Processor 106 is configured to receive input 120 regarding exam parameters. In an embodiment, the exam parameters include luminance 121 and luminance contrast 123 of monitor 15 (illustrated in FIG. 1) and letter size input 125. The desired font size of the sentence that will be displayed on monitor 15 is provided by letter size input 125. Input 120 is provided by the operator for inputting to computer 101 through GUI device 102.

Processor 106 is configured to select a visual indicium from inventory 116, preferably a sentence including a plurality of words, display it on display component 10 for the subject to read, and display a copy of the visual indicium in a word verification box on GUI device 102. The sentence and its copy are displayed on both display component 10 and GUI device 102, respectively, in the same word order. However, if the visual indicium is a series of Landolt C's, for example, the series of Landolt C's and its copy will be displayed on display component 10 and GUI device 102, respectively, in the same display order. Processor 106 is configured to display the words on GUI device 102 as selectable objects in order to provide input 122. Processor 106 is configured to receive input 122 from GUI device 102 regarding a selection number of words misread by the subject in order to adjust the calculation of the reading rate, which processor 106 is configured to display on the GUI device 102 as rate 124 in words per minute and rate 126 in characters per minute.

Processor 106 is configured to receive input 115 delineating the start of a new, or first, data run and to receive input 127 delineating the end of the data run. Both inputs 115 and 127 are provided by the operator for inputting to computer 101 through GUI device 102. Input 115 enables processor 106 to receive camera input 117, and microphone input 119 and display real-time information 111 on GUI device 102 for the operator to see. Information 111 includes the reading distance 130 and angle 132, which is the angle the subject is from a perpendicular line to monitor 15 (illustrated in FIG. 1). Both reading distance 130 and angle 132 are provided by camera input 117.

During the data run, processor 106 is configured to display sound wave graph 134 generated from microphone input 119, and distance graph 136 generated from camera input 117 on GUI device 102. At the completion of the data run, as is indicated by input 127, processor 106 is configured to calculate and display information 133 on GUI device 102. Information 133 includes time 128, reading rate 124 in words per minute, reading rate 126 in characters per minute, average distance 131, and log MAR 138. Time 128 is the amount of time the subject takes to read the sentence displayed to him or her and is calculated based on the temporal starting and stopping points determined by microphone input 119.

Still referring to FIG. 2, processor 106 is configured to provide and display direction 150 on GUI device 102, and receive test input 151 regarding the calibration of camera input 117. Test input 151 is provided by camera input 117 in a series of measurements such as measurements 152 and 153. Briefly, as this will be described in more detail below with respect to FIGS. 3 to 6B, direction 150 prompts the operator to position a phantom subject, such as a brick or pole, at a certain distance away dictated by one of the default reading distance values stored in settings 114 of memory unit 104 (such as 40 cm away). The phantom has a reflective tag, such as tag 16 illustrated in FIG. 1, attached to it so that processor 106 can receive camera input 117 for measurement 152. Direction 150 then prompts the operator to position the phantom another distance away dictated by another one of the default reading distance values stored in settings 114 of memory unit 104 (such as 80 cm away) and processor 106 receives measurement 153. Measurements 152 and 153 constitute count 180, or in other words the first count of three counts. Processor 106 is configured to then compare a calculated reading distance for each of measurements 152 and 153 and update the default reading values stored in settings 114 in memory unit 104, thereby calibrating camera input 117. Preferably, processor 106 is configured to receive multiple counts 180 and offset the default reading values in settings 114 according to an average measurement 152 and an average 153, as will be described in more detail below with respect to FIGS. 3 to 6B.

It is possible for the cameras 17a and 17b, shown in FIG. 1, to shift out of calibration during shipping or through rough handling in the clinic environment. It is recommended that the factory calibration is checked during installation. In the event the factory calibration is not accurate, the SRD can be recalibrated using Auto-Calibration software.

Figure 3:
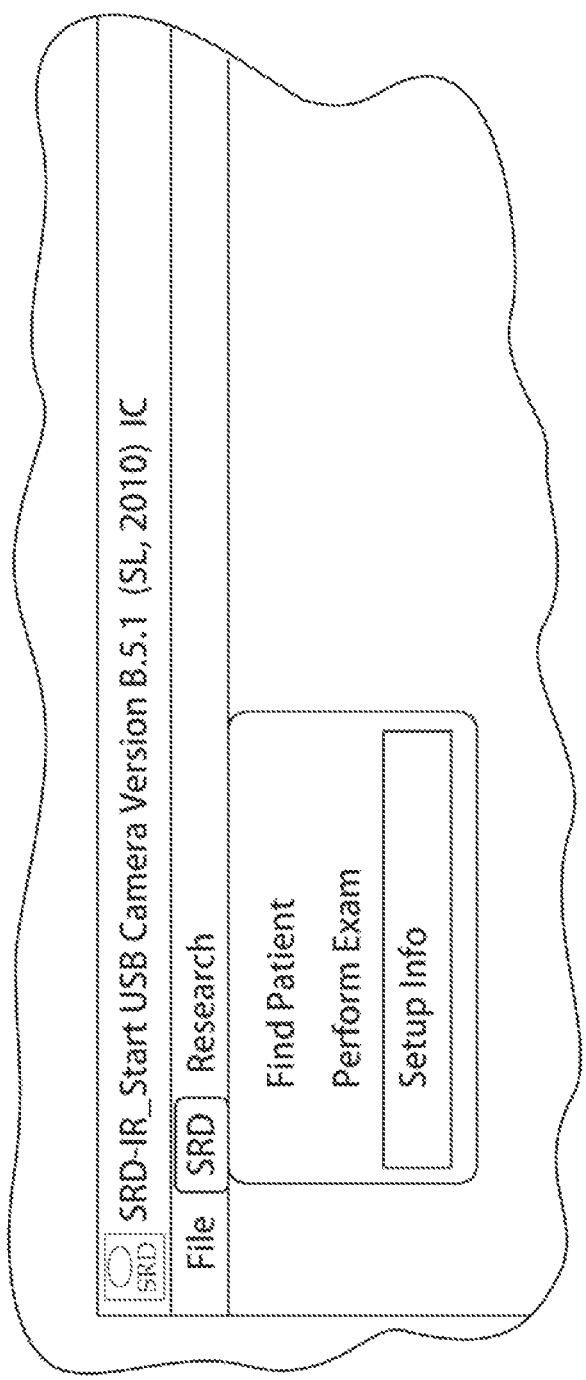
FIG. 3 is a partial screen shot of the Salzburg Reading Desk (hereinafter "SRD") start-up menu.
Figure 4:
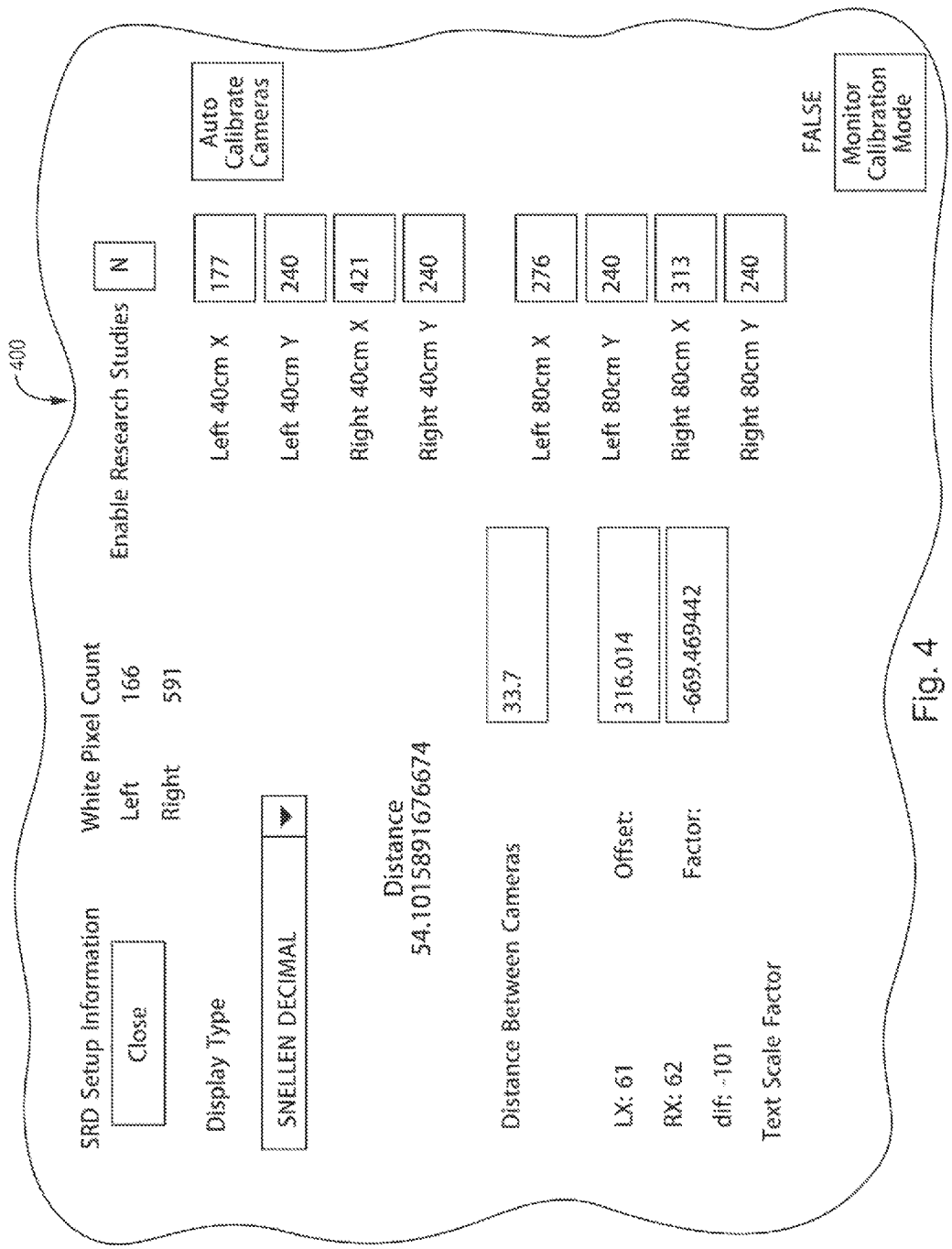
FIG. 4 is a partial screen shot of the SRD set-up information window showing a real-time distance measurement from the cameras.

To auto-calibrate the distance measurements provided by cameras 17a and 17b, shown in FIG. 1, the user selects the <Setup Info> option from the start-up screen shown in FIG. 3, and the SRD Setup window 400 will be displayed to the operator as is shown in FIG. 4. SRD Setup window 400 displays a real-time distance value to aid the operator in determining whether the distance measurements initially fall within those accuracy levels. When the distance measurements are properly calibrated, the real-time distance measurements displayed will fall within an accuracy level. Preferably, ±5 mm is the accuracy level for a distance measurement of 25 cm, and ±2 mm is the accuracy level for distance measurements of 30 cm, 40 cm, 50 cm, 60 cm, 70 cm and 80 cm.

To determine whether the distance measurements initially fall within the above described accuracy levels, the operator adjusts angle α (shown in FIG. 1) so that monitor 15 is perpendicular to the flat surface it is sitting on. Then, the operator uses a measuring tape and makes marks at 30 cm, 40 cm, 50 cm, and 80 cm directly in front of monitor 15. The operator places an adhesive reflective tag on a phantom subject, such as a brick or a pole, and places the phantom at the measured marks of 30 cm, 40 cm, 50 cm, and 80 cm directly in front of monitor 15. The operator looks at the displayed real-time distance value while the phantom is at each of the measured marks to see if the distance measurements fall within the appropriate accurate level.

Figure 5A:
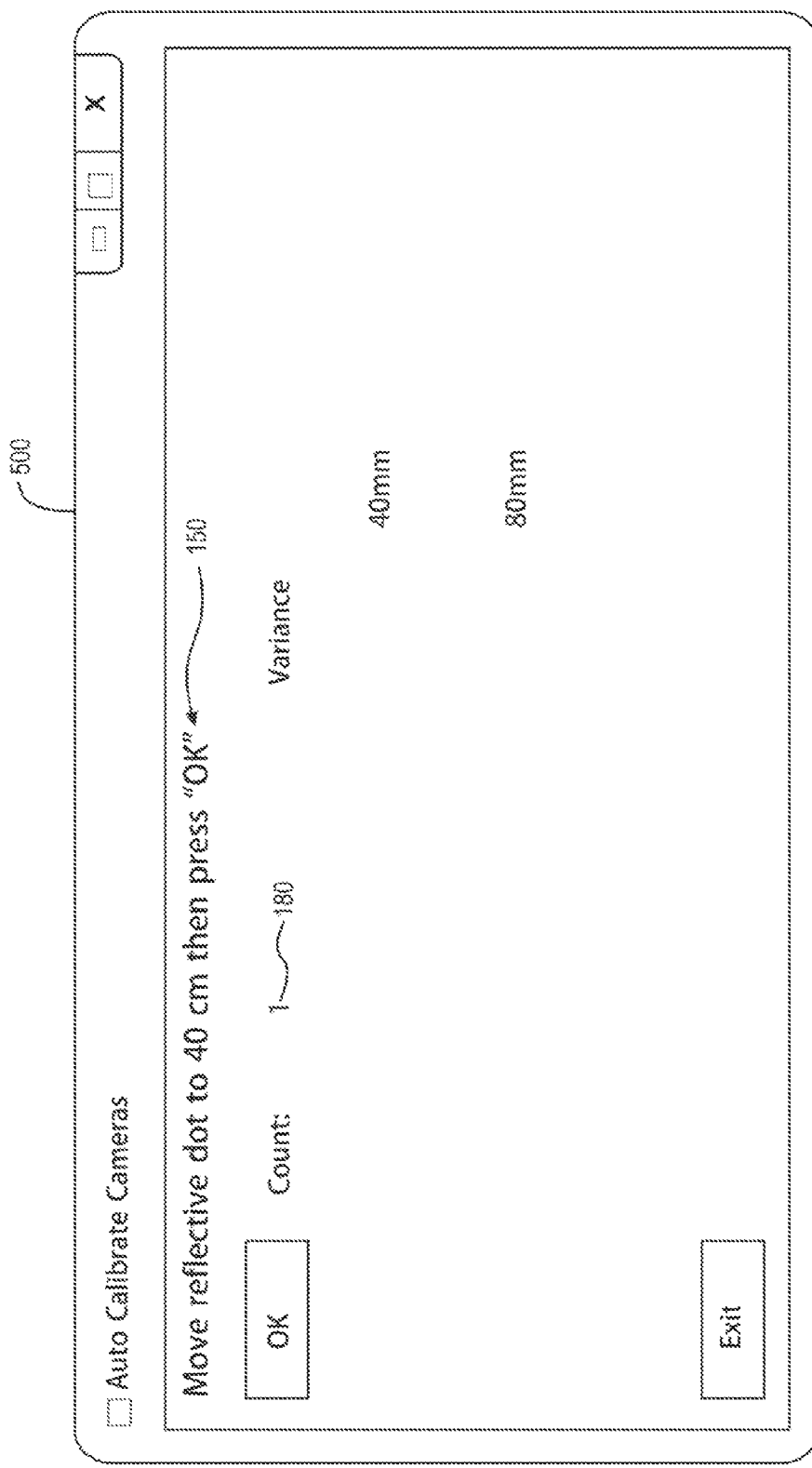
FIG. 5A is a pop-up window display prompting the first measurement of a count during autocalibration.

If the real-time distance value displayed in SRD Setup window 400 in FIG. 4 does not fall within the appropriate accuracy level for any of the measured distances designated by the marks, then the operator simply clicks the <Auto Calibrate Cameras> button and window prompt 500 will show up as can be seen in FIG. 5A. Window prompt 500, as will be described below, is the first measurement of the first count. Preferably, the auto-calibration method comprises three counts with two measurements per count.

FIG. 5A illustrates pop-up window prompt 500 for the first measurement 152 in test input 151 as was described above with reference to FIG. 2. Window prompt 500 in FIG. 5A displays direction 150 to the operator by displaying "Move reflective dot to 40 cm then press "OK"". The reflective dot is the reflective tag that has been referred to, and 40 cm is one of the default reading distances stored in settings 114 (found in FIG. 2). Window prompt 500 also displays count number 180 so that the operator does not need to keep track of it him- or herself. In this instance, Figure SA shows window prompt 500 as prompting the first measurement of count 1. Once the phantom is placed 40 cm away, the operator activates the <OK> button using the pointing device and window prompt 550 (shown in FIG. 5B) will pop-up for the second measurement of count 1. Activating the <OK> button provides the vertical and horizontal displacement values of the tag as measurement 152 in input 151 (found in FIG. 2) and provides another window prompt that is shown in FIG. 5B.

Figure 5B:
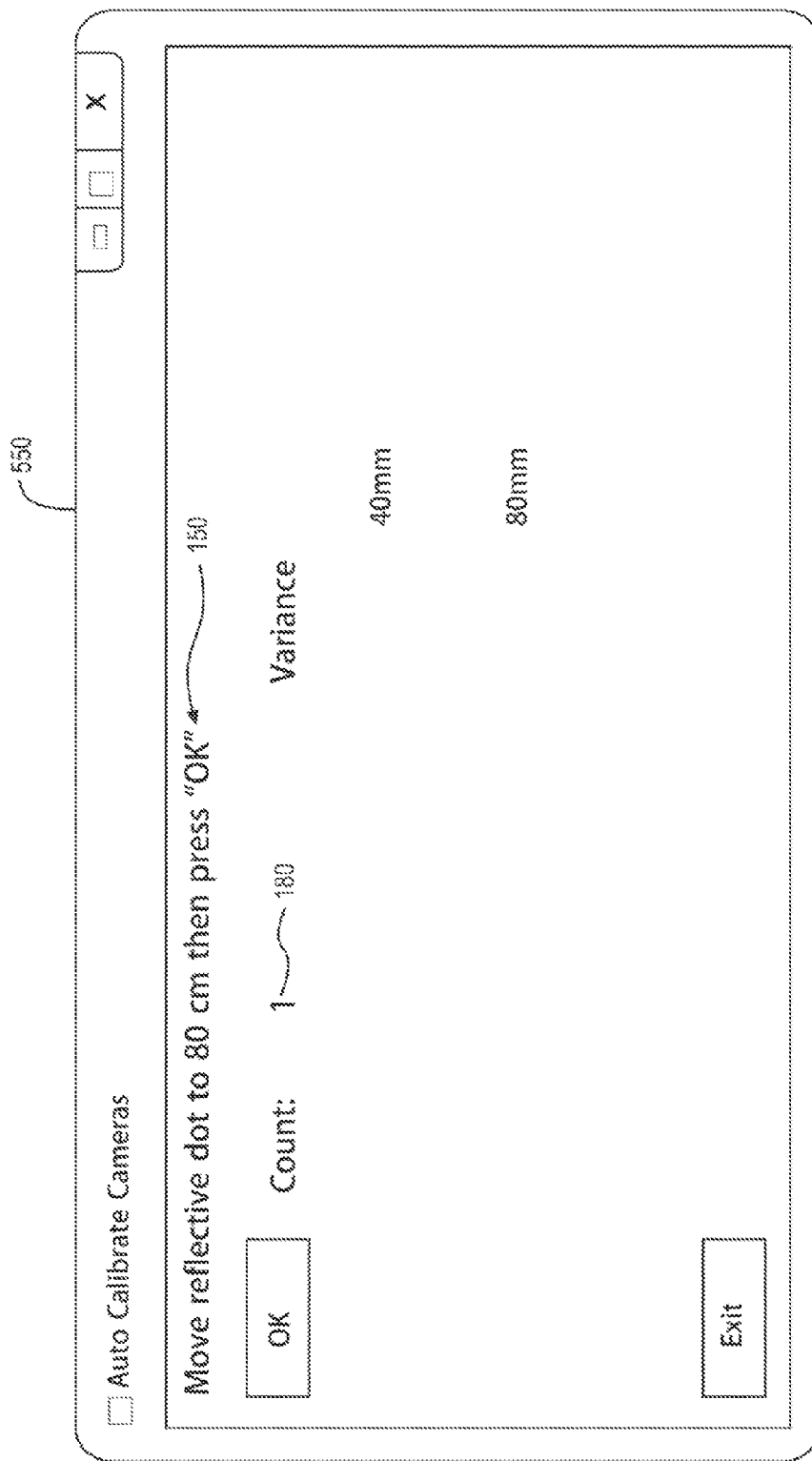
FIG. 5B is a pop-up window display prompting the second measurement of a count during autocalibration.

FIG. 5B illustrates pop-up window prompt 550 for the second measurement 153 in test input 151 as was described above with reference to FIG. 2. Window prompt 550 in FIG. 5B displays direction 150 to the operator by displaying "Move reflective dot to 80 cm then press "OK"". The reflective dot is, again, the reflective tag that has been referred to, and 80 cm is one of the default reading distances stored in settings 114 (shown in FIG. 2). Window prompt 550 also displays count number 180 so that the operator does not need to keep track of it him- or herself. In this instance, FIG. 5B shows window prompt 550 as prompting the second measurement of count 1. Once the phantom is placed 80 cm away, the operator activates the <OK> button using the pointing device and provides the vertical and horizontal displacement values of the tag as measurement 153 in input 151 (found in FIG. 2). Also, activating the <OK> button will provide another window prompt prompting the operator to "Move reflective dot to 40 cm then press "OK"" for the first measurement of count 2.

Figure 6A:
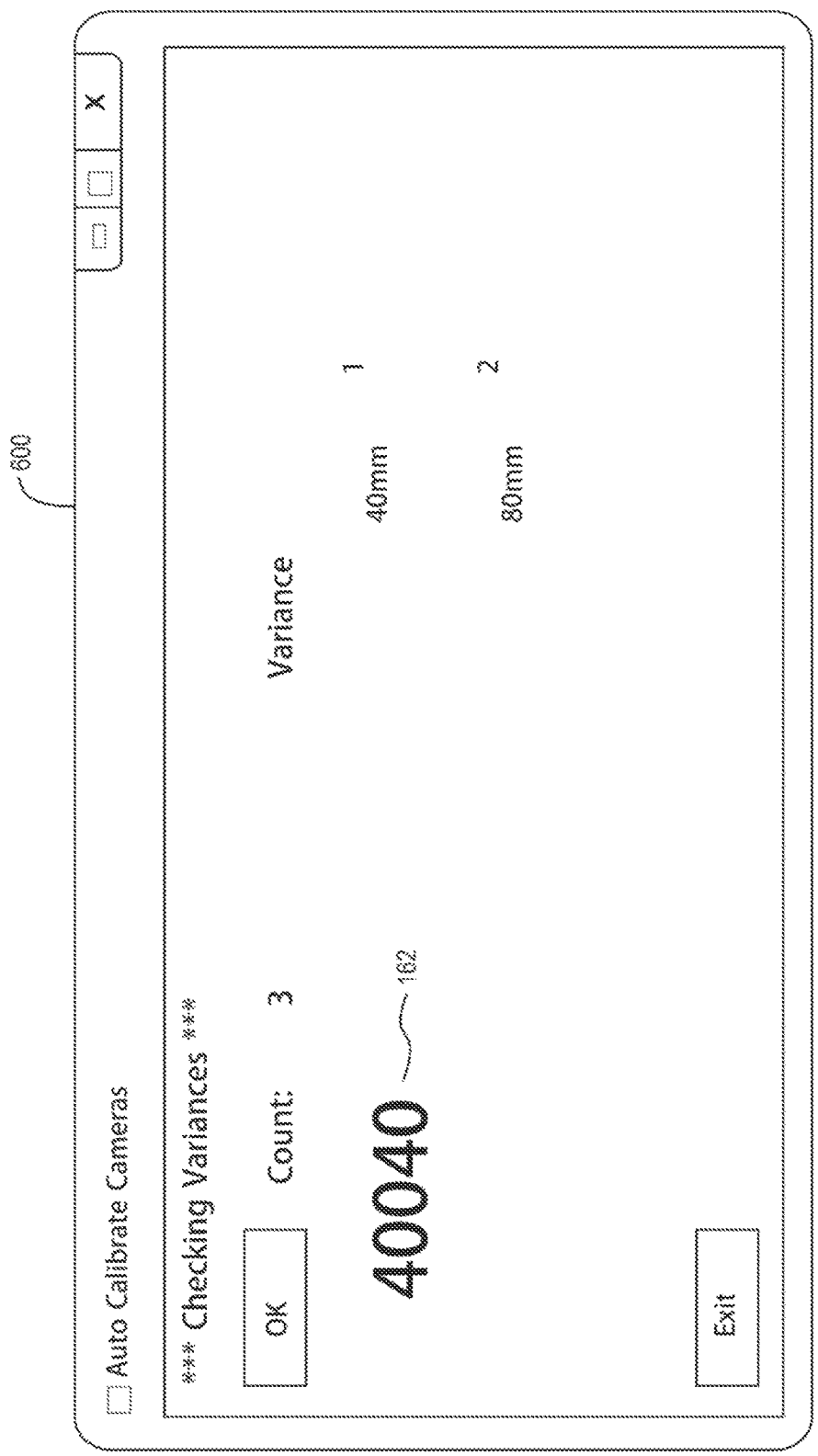
FIG. 6A is a pop-up window display as the computer auto-calibrates the camera.

FIG. 6A illustrates pop-up window 600, which is presented to the operator to signal that no more measurements are needed. Preferably, three counts of two measurements are taken with each measurement returning horizontal and vertical displacement values. Pop-up window 600 is presented to the operator while the computer software calibrates the distance measurements, with ticker 162 counting down the estimated time left until the calibration is complete. Ticker 162 is generally counting down to, and stops at, 40001.

Generally, the computer software averages all of the vertical and horizontal displacement measurements at 40 cm (in other words, the first measurements of each count), averages all of the vertical and horizontal displacement measurements at 80 cm (in other words, the second measurements of each count), and then compares a calculated reading distance from each of the averaged vertical and horizontal displacements at 40 cm and 80 cm to the default reading distances (40 cm and 80 cm) stored in settings 114 (found in FIG. 2). The default reading values stored in settings 114 are updated accordingly.

Figure 6B:
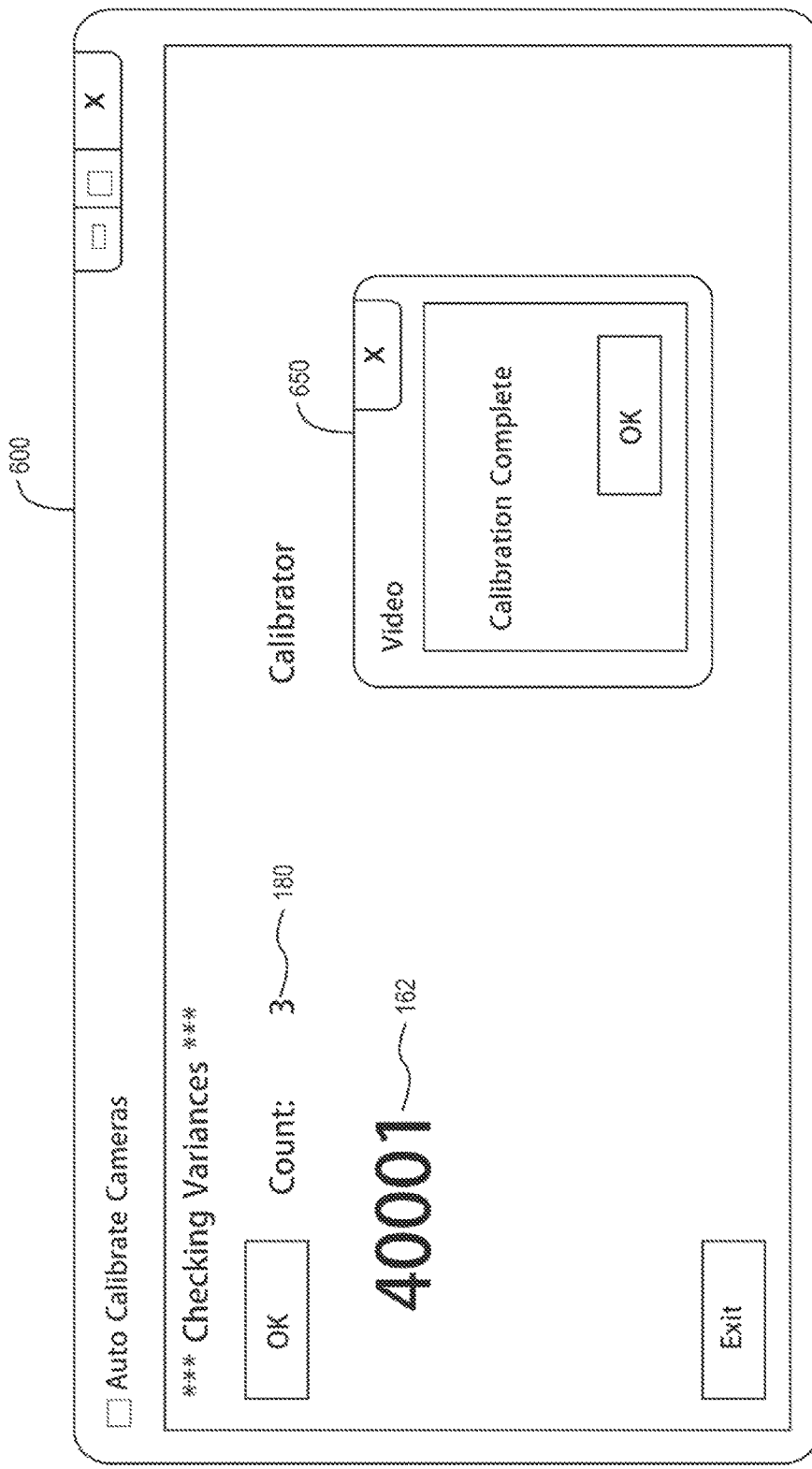
FIG. 6B is a pop-up window display when the computer has finished auto-calibrating the camera.

FIG. 6B illustrates ticker 162 having reached its end at 40001 and dialogue box 650 indicating that calibration is complete. If the calibration was unsuccessful, then a dialogue box will appear that says "Unable to Calibrate" and the operator will have to start the auto-calibration process over again.

Measuring and control software controls the procedure of the vision determination. It is preferably designed in such a way that the lead investigator can be guided through the experiment with the simple push of a button or via mouse clicks, wherein none of the required inputs may be forgotten on the one hand and the result is automatically archived and printed out on the other hand. Preferably, the computer provides optical and/or acoustic step-by-step instructions throughout the entire process. This reduces the training time for the operating staff and additionally prevents errors during the vision determination. With another model, it is possible to conduct the experiment automatically without the required attendance of the lead investigator.

As seen in FIG. 3, the program has a start-up screen with a tab that allows the operator to choose among finding patient records, performing the exam, and access the program setup information. In order to calibrate cameras 17a and 17b (shown in FIG. 1), the operator activates the <Setup Info> option. In order to administer an exam on a subject, the operator activates the <Find Patient> option, which enables the operator to either find the medical records of an already existing patient or to create a medical record of a new patient. The <Perform Exam> option is disabled until a patient's medical record is activated.

FIG. 7A illustrates Patient Search window 300 that is displayed on monitor 25 (shown in FIG. 1) after activating the <Find Patient> option (shown in FIG. 3). The Patient Search window displays search criteria box 302 to efficiently find the medical records for existing patients by Patient ID number or Last Name. Patient data box 310 has a plurality of fillable fields that are initially blank, and a <Perform SRD Exam> button that is initially disabled until a patient is chosen from patient database box 304. In the instance of a new patient, the operator simply types in the last name, first name and birth date into the fillable fields of patient data box 310 and activating the <Add New Patient> button. The fillable fields of patient data box 310 provide input 110 and can be stored as part of EMR 112 as seen in FIG. 2.

Figure 7B:
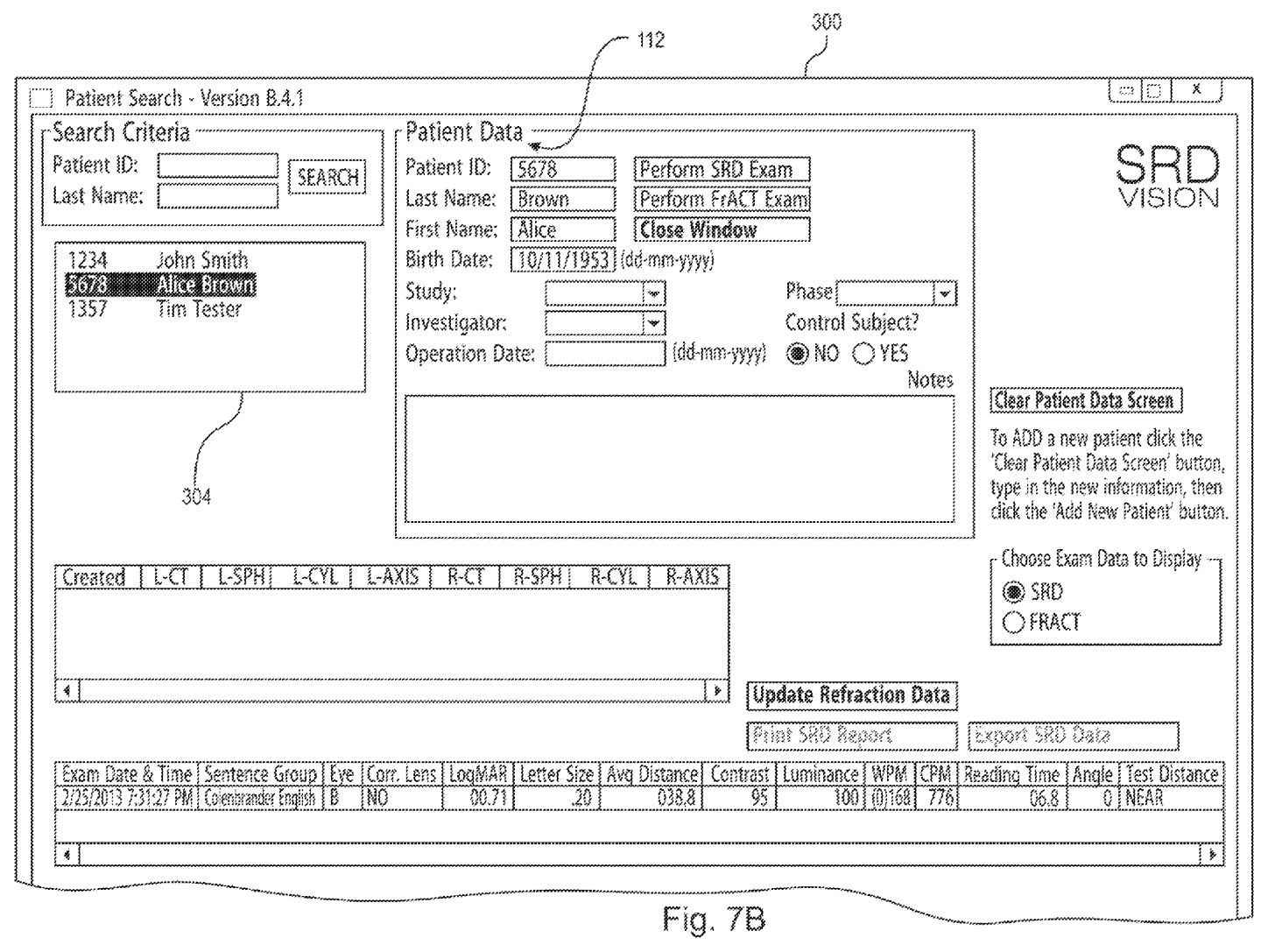

FIG. 7B illustrates Patient Search window 300 with a patient selected from patient database 304 and the <Perform SRD Exam> button now enabled. The fillable fields of patient data box 310 are automatically retrieved from EMR 112 (shown in FIG. 2) and filled in.

Figure 8:

FIG. 8 illustrates SRD Exam window 800 that is displayed on computer 20 after activating the <Perform SRD Exam> button from patient search window 300 shown in FIG. 7A. However, sound wave graph 134 and reading distance graph 136 remain blank until a later point, as will be described in more detail below. Exam parameters box 820 contains a plurality of pull-down menus, one of which enables the operator to control the font size of the displayed sentence by choosing an option from the <Select Letter Size> pull-down menu. Preferably, the size options are in either the Snellen x/20 format followed by the United States, Snellen x/6 format followed by the United Kingdom, or the Decimal format followed by Europe. Exam parameter box 820 also includes a pull-down menu labeled <Select Sentence Group>, which controls what type of sentence will appear on monitor 15. Each sentence group, such as Colenbrander English or Colenbrander French, is stored in inventory 116 in FIG. 2. It should be appreciated that any type of sentence group can be stored in inventory 116 and the current invention is not limited to storing and displaying Colenbrander sentence groups. Further, a plurality of sentence groups can be stored in a plurality of inventories.

Other options in exam parameters box 820 includes the luminance and contrast of monitor 15 (shown in FIG. 1). Most exams are conducting with the luminance set at 100%, with 100%=300 candela per meter squared. The contrast parameter is based on a Michelson Contrast formula and is offered with options on a scale of contrast percentages with 100% being the highest contrast. Exam parameters box 820 also includes pull-down menus enabling the operator to provide input as to which eye the exam is being conducted under (with the left eye, right eye, or both eyes as viable options), whether the subject is using corrective lenses (yes and no as viable options), and the test distance (with near distance and intermediate distance as viable options). The near distance option is where sentences are sized for a 40 cm distance from monitor 15 (shown in FIG. 1), and the intermediate distance is where sentences are sized for a 80 cm distance from monitor 15.

To conduct an exam, the operator or the subject places tag 16 (shown in FIG. 1), which is preferably a reflective dot, between the subject's eyes just above the bridge of his or her nose or on his or her eye glasses. The subject is then positioned to the desired testing distance, either near or intermediate as was chosen in the exam parameters. Again, near distance is the distance at which the subject normally reads, which is typically between 30 cm and 50 cm, and the intermediate distance is approximately 80 cm. Still referring to FIG. 8, a real-time distance value is displayed in SRD exam window 800 to facilitate the initial positioning of the subject and to check that the cameras are responding. The sound and distance measurements for the exam are initiated with the <Start> button and are subsequently displayed on SRD exam window 800. Selecting the <Start> button also displays the sentence that was chosen from the inventory onto both monitor 15 and computer 20. The sentence will be displayed on monitor 15 (shown in FIG. 1) with the font or letter size that was chosen by the operator in exam parameters box 820. Monitor 15 will also have the luminance and contrast as was chosen in exam parameters box 820.

While the sentence is displayed to the subject on monitor 15, the sentence is also displayed to the operator in word verification box 850 in SRD exam window 800 shown in FIG. 8 with each word of the sentence as a selectable object for the operator to interact with individually. This enables the operator to follow along while the subject is reading the sentence (especially if the sentence has a small letter size and cannot be seen on monitor 15 from the operator's position) and activate whichever word or words the subject misreads by clicking on the word in word verification box 850. With the operator selecting the misread words as they are misread by the subject, computer 20 (shown in FIG. 1) keeps track of the misread words for the operator, and, therefore cuts down on the total length of the time it takes to administer the exam as well as cutting down on operator error in calculating visual acuity. Visual acuity is calculated from the reading rate, v (indicated as wpm=words per minute), which is calculated according to v=60 w/t where w is the number of words in the sentence and t is the time in seconds it takes for the subject to read that number of words. Therefore, displaying each word as a selectable object to the operator enables computer 20 to subtract the number of selected words from the total number of words presented to the subject in order to automatically adjust the w variable for calculating the reading rate.

It is possible for computer 20 to be programmed with voice recognition software that can recognize any misread words without the need of an operator to provide the input.

An average reading distance is also calculated by computer 20. The respective image coordinates of the center point of tag 16 (shown in FIG. 1) are determined by both cameras 17a and 17b. The color of tag 16 must not appear elsewhere in the image. Using these image coordinates, the camera distance and the camera output scale, the program calculates the spatial coordinates of the position of tag 16 by means of stereophotogrammetry in a second step. In the next step, the distance of tag 16 from the reading line, whose coordinates are known to the program, is calculated. The result is illustrated as a number value in its output box and illustrated graphically in graph 136 in SRD exam window 800 in FIG. 8. This process is repeated constantly, for at most 25 seconds or it is terminated by pressing the <Stop> button.

The measuring procedure is terminated after the subject has finished reading. Then the average value of the measured distances is calculated, displayed as a value in the output box and illustrated as horizontal line in the distance diagram.

The reading duration is determined by microphone 19 (shown in FIG. 1) as was described above. A sound wave appears in graph 134 in SRD exam window 800 as the subject speaks. The reading duration can be adjusted by the operator in SRD exam window 800 shown in FIG. 8 by clicking and dragging the two measuring lines 831 and 832 in graph 134. The measuring tags run synchronously in both graph 134 and graph 136. At the same time as a measuring line is being dragged, the average value of the measured distance values within this range is re-calculated and displayed as a value on SRD exam window 800. The values for the reading speed and the reading acuity are also re-calculated and displayed according to the adjusted time range. By adjusting the reading time by pulling either or both measuring lines 831 and 832, it is then possible to save the data set and the following calculated data is displayed on SRD exam window 800: reading rate in wpm (words/min), Log MAR, reading time, and average distance. If the subject read the sentence very quickly, the operator may not want to save the data and can activate the <Clear Graph> button. If the subject read the sentence slowly, or the subject's reading speed starts to slow between successive data runs, or as deemed fit by the operator, the operator can save the data by activating the <Store Data> button. The data related to the displayed sentence will be saved to computer 20.

The distance corrected vision in form of a log MAR factor is calculated according to:

$$\log MAR = 1.2 - 0.1 \times SN + \log_{10}(40/\text{Distmv})$$

where SN is the sentence number of the reading chart based on the letter size of the visual indicia, and Distmv is the average value of the measured reading distance in centimeters.

Generally, an exam comprises a plurality of data runs with the operator selecting smaller and smaller letter sizes for each successive data run. Initially, the operator determines a reading speed that should indicate the subject's reading acuity relative to the subject's condition, and then conducts a succession of data runs with sentences having smaller and smaller letter sizes until the subject's reading speed matches the initially determined reading speed. For example, some medical health professionals believe that in patients with a healthy eye, 80 words per minute is the lowest acceptable recreational reading speed. For a patient with a retinal pathology, a lower reading speed such as 40 words per minute may be the objective.

With an exam generally including multiple data runs selecting sentences from the inventory, system 100 further includes computer readable instructions designed to avoid presenting a sentence that was recently presented. This way, the subject will not be biased with a memory of a previously presented sentence at a larger font size while reading at a smaller font size. The computer readable instructions also select the sentences at random from the inventory.

Data runs are stored as part of the EMR of the patient. The data runs that represent all of the sentences that have been recorded can be seen in patient search window 300 below patient database 304 in FIG. 7B. The operator can scroll across the data runs and see all of the past exams.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention as claimed.

LIST OF REFERENCE NUMBERS

10 Display component
11 Subject
15 Monitor
16 Tag
17 Camera
19 Microphone
20 Specially programmed computer
24 Data interface
25 User screen
30 Base
40 Visual indicium
50 Word verification box
102 Graphical user interface (GUI) device
104 Memory unit
106 Processor
108 Computer readable instructions
110 Input identifying patient
112 Electronic medical records
114 Settings
115 Input to start data run
116 Inventory
117 Input from camera
118 Information (displacement data)
119 Input from microphone
120 Input about exam parameters
122 Input about reading rate
124 Information about reading rate wpm
126 Information about reading rate cpm
128 Information about reading time (real time)
130 Information about distance (real time)
132 Information about angle (real time)
134 Graph of sound wave
136 Graph of distance
138 Information log MAR
150 Direction (autocalibrate)
151 Test input
152 Test input measurement 1 C1
153 Test input measurement 2 C1
162 Ticker
180 Count number
300 Patient Search Window
302 Patient search
304 Patient Database
310 Patient data box
400 SRD Setup Window
500 pop-up window prompt
550 pop-up window prompt 600 pop-up window
650 dialogue box
800 SRD Exam window
820 Exam parameters box
831 measuring line
832 measuring line
850 Word verification box
α Angle
D Reading distance

What is claimed is:

1. A computer-based system for calculating a log MAR value for a reading acuity test, comprising:
   receiving an inventory of words from a user;
   storing said inventory of words in a database;
   randomly selecting a plurality of words from said inventory of words;
   a means for displaying said plurality of words in a font size on a first monitor, where said plurality of words will be read aloud by a first person taking said test;
   a means for displaying a copy of said plurality of words on a second monitor, where said plurality of words will be observable by a second person, and each of said plurality of words is selectable by said second person using a pointing device, such that said second person may select any of such words that are read incorrectly by said first person;
   a means for measuring the amount of time said first person takes to read said plurality of words on said first monitor;
   a means for calculating a reading rate based upon said plurality of words and said amount of time, where said reading rate is modified in accordance with the number of words selected by said second person as read incorrectly;
   a means for measuring a distance between said first person and said first monitor, said means for measuring said distance comprising photogrammetry; and,
   a means for calculating said log MAR value based upon said distance, said font size and said reading rate.

2. The computer-based system of claim 1, further comprising a means for adjusting an angle of inclination of said first monitor.

3. A computer-based system for calculating a log MAR value for a reading acuity test, comprising:
   receiving an inventory of sentences from a user;
   storing said inventory of sentences in a database;
   a means for selecting a sentence randomly from said inventory of sentences;
   a means for displaying said sentence in a font size on a first monitor, where said sentence will be read aloud by a first person taking said test;
   a means for displaying a copy of said sentence on a second monitor;
   a means for measuring the amount of time said first person takes to read said sentence on said first monitor;
   a means for calculating a reading rate based upon said sentence and said amount of time;
   a means for measuring a distance between said first person and said first monitor, said means for measuring said distance comprising photogrammetry; and,
   a means for calculating said log MAR value based upon said distance, said font size and said reading rate.

4. The computer-based system of claim 3, further comprising a means for adjusting an angle of inclination of said first monitor.

5. A computer-based system for calculating a log MAR value for a reading acuity test, comprising:
   receiving an inventory of words from a user;
   storing said inventory of words in a database;
   randomly selecting a plurality of words from said inventory of words;
   a means for displaying said plurality of words in a font size on a first monitor, where said plurality of words will be read aloud by a first person taking said test;
   a means for displaying a copy of said plurality of words on a second monitor;
   a means for measuring the amount of time said first person takes to read said plurality of words on said first monitor;
   a means for calculating a reading rate based upon said plurality of words and said amount of time;
   a means for measuring a distance between said first person and said first monitor, said means for measuring said distance comprising photogrammetry;
   a means for automatically calibrating said means for measuring said distance between said first person and said first monitor; and,
   a means for calculating said log MAR value based upon said distance, said font size and said reading rate.

6. The computer-based system of claim 5, further comprising a means for adjusting an angle of inclination of said first monitor.

7. A method of calculating a log MAR value for a reading acuity test, comprising the following steps:
   receiving an inventory of words from a user;
   storing said inventory of words in a database;
   randomly selecting a plurality of words from said inventory of words;
   displaying a plurality of words in a font size on a first monitor, where said plurality of words will be read aloud by a person taking said test;
   displaying a copy of said plurality of words on a second monitor, where said plurality of words will be observable by a second person, and each of said plurality of words is selectable by said second person using a pointing device, such that said second person may select any of such words that are read incorrectly by said first person;
   measuring the amount of time said first person takes to read said plurality of words on said first monitor;
   calculating a reading rate based upon said plurality of words and said amount of time, where said reading rate is modified in accordance with the number of words selected by said second person as read incorrectly;
   photogrammetrically measuring a distance between said first person and said first monitor; and,
   calculating said log MAR value based upon said distance, said font size and said reading rate.

8. The method of claim 7, wherein the plurality of words is grouped as a sentence, the method further comprising the step of selecting a sentence randomly from an inventory of sentences.

9. The method of claim 7, further comprising the step of automatically calibrating said distance between said first person and said first monitor.

* * * * *